United States Patent
Giroud et al.

(10) Patent No.: US 8,377,427 B2
(45) Date of Patent: Feb. 19, 2013

(54) COSMETIC COMPOSITION BASED ON NANOPARTICLES AND ON WATER-SOLUBLE ORGANIC SILICON COMPOUNDS

(75) Inventors: Franck Giroud, Clichy (FR); Henri Samain, Bievres (FR); Isabelle Rollat, Paris (FR)

(73) Assignee: L'Oreal, Paris (FR)

( * ) Notice: Subject to any disclaimer, the term of this patent is extended or adjusted under 35 U.S.C. 154(b) by 1773 days.

(21) Appl. No.: 10/240,195

(22) PCT Filed: Mar. 29, 2001

(86) PCT No.: PCT/FR01/00952
§ 371 (c)(1), (2), (4) Date: Jun. 9, 2003

(87) PCT Pub. No.: WO01/74308
PCT Pub. Date: Oct. 11, 2001

(65) Prior Publication Data
US 2004/0013632 A1    Jan. 22, 2004

(51) Int. Cl.
*A61K 8/00* (2006.01)
(52) U.S. Cl. ..................................................... 424/70.1
(58) Field of Classification Search .................. None
See application file for complete search history.

(56) References Cited

U.S. PATENT DOCUMENTS

| 3,689,300 | A | * | 9/1972 | Bunger et al. ............. 106/287.1 |
| 4,344,763 | A |   | 8/1982 | Tolgyesi |
| 5,310,845 | A | * | 5/1994 | Raleigh et al. .................. 528/18 |
| 5,695,747 | A | * | 12/1997 | Forestier et al. ................ 424/59 |
| 5,919,487 | A |   | 7/1999 | Simonnet |
| 6,607,994 | B2 | * | 8/2003 | Soane et al. .................... 442/59 |

FOREIGN PATENT DOCUMENTS

| EP | 159928 | 10/1985 |
| EP | 832943 | 4/1998 |
| EP | 1064918 | 1/2001 |
| FR | 2751572 | 1/1998 |
| FR | 2779637 | 12/1999 |
| FR | 2783164 | 3/2000 |

OTHER PUBLICATIONS

Patent Abstracts of Japan vol. 13, No. 171, Apr. 24, 1989 & JP 64 000126 A (Jan. 5, 1989).
Patent Abstracts of Japan vol. 1996, No. 2, Feb. 29, 1996 & JP 07 267640 (Oct. 17, 1995).

* cited by examiner

*Primary Examiner* — Paul Dickinson
(74) *Attorney, Agent, or Firm* — Nixon & Vanderhye P.C.

(57) ABSTRACT

The invention concerns a composition comprising, in a cosmetically acceptable medium containing water and/or a solvent, metal, metal oxide, metal carbide or nitride nanoparticles or mixtures thereof, and one or several organic silicon compounds soluble in water and/or in the solvent, having one, two or three silicon atoms, and at least two hydroxyl or hydrolysable groups per molecule. The invention is applicable to hair care compositions.

6 Claims, No Drawings

COSMETIC COMPOSITION BASED ON NANOPARTICLES AND ON WATER-SOLUBLE ORGANIC SILICON COMPOUNDS

This application is the U.S. national phase of international application PCT/FR01/00952 filed 29 Mar. 2001, which designated the U.S.

The present invention relates generally to aqueous cosmetic compositions, in particular for treating the hair, comprising nanoparticles and water-soluble organosilicon compounds.

Styling products exist which are used for increasing the volume of the hairstyle. These products, based on film-forming polymers, are particularly appreciated by users with fine hair.

These styling products leave a somewhat unnatural feel resulting from the deposition of polymer on the surface of the hair.

It is moreover possible to use permanent-waving treatments. These treatments, based on the use of a reducing agent and an oxidizing agent, require the hair to be placed under mechanical tension by means of rolling equipment, to give the head of hair a long-lasting shape. This process does indeed make it possible to increase the volume of the head of hair. However, these treatments have the drawback of modifying the appearance of the hair (curly hair) and of degrading the condition of the fibers.

No treatment exists for increasing the volume of the head of hair without modifying the shape or feel of the hair.

It has now been discovered, surprisingly, that it is possible to increase the volume of the head of hair without modifying the shape or feel of the hair, by using specific compositions described below.

With these compositions, the body of the hairstyle can be increased, without impairing the feel of the hair or its shape, without degrading the fibers and without adhesion between the hairs by a film-forming material.

Moreover, it has also been found that the use of these compositions makes the hair feel thicker (although the thickness of the hairs has not been increased). This observation is particularly advantageous since many users appreciate this sensation of fortified hair.

According to the invention, the compositions are characterized in that they contain, in a cosmetically acceptable medium comprising water and/or at least one solvent, i) nanoparticles chosen from metallic nanoparticles, of metal oxides, of metal carbides or nitrides and mixtures thereof, and ii) one or more organosilicon compounds that are soluble in the cosmetically acceptable medium, chosen from organosilanes comprising one, two or three silicon atoms and organosiloxanes comprising two or three silicon atoms, the silicon compounds also comprising two hydrolyzable or hydroxyl groups per molecule.

The term "nanoparticles" means particles less than 200 nm and preferably less than 50 nm in size.

Among the metal oxide nanoparticles that may be mentioned are cerium oxide (CeO), alumina ($Al_2O_3$), titanium oxide ($TiO_2$), titanates ($BaTiO_3$, $Ba_{0.5}Sr_{0.5}TiO_3$, $SrTiO_3$), indium oxide ($In_2O_3$), tin oxide ($SnO_2$), antimony oxide ($Sb_2O_3$), magnesium oxide (MgO), calcium oxide (CaO), manganese oxides ($Mn_3O_4$, $MnO_2$), molybdenum oxide ($MoO_3$), silica ($SiO_2$), zinc oxide (ZnO), yttrium oxide ($Y_2O_3$), etc., and mixtures thereof.

Among the metallic nanoparticles that may be mentioned are nanoparticles of silver, gold, platinum, indium, etc., and mixtures thereof.

Among the metal carbides and nitrides that may be mentioned are silicon carbide (SiC) and silicon nitride ($Si_3N_4$).

Preferably, the nanoparticles are alumina nanoparticles.

The amount of nanoparticles in the compositions generally ranges from 0.01% to 30% by weight and preferably from 0.05% to 5% by weight, relative to the total weight of the composition.

The second essential constituent of the compositions of the invention is the silicon compound(s), which may be sparingly polymerized or unpolymerized, and soluble in the cosmetically acceptable medium and more particularly in water and/or the solvent(s) of this medium.

As mentioned previously, the organosilicon compounds are chosen from organosilanes that are soluble in water and/or solvents, comprising one, two or three silicon atoms, and organosiloxanes that are soluble in water and/or solvents, comprising two or three silicon atoms, preferably two silicon atoms, these compounds also comprising at least two hydrolyzable or hydroxyl groups per molecule.

Preferably, the organosilicon compounds of the invention comprise three hydrolyzable and/or hydroxyl groups per molecule. The preferred hydrolyzable groups are chosen from alkoxy, aryloxy and halogen groups.

The organosilicon compound can bear one or more functions making it compatible with water and/or solvents, and/or giving it affinity with keratin fibers.

Preferably, the organosilicon compound bears one or more solubilizing functions, which in particular improve the solubility in water, for example basic functions such as alkylamine and alkylpolyamine functions, and nonbasic functions such as alkyl alcohol, alkylthiol, alkyl acid, alkylpolyol and alkylpolycarboxylic functions.

Among the solubilizing functions, the preferred functions are basic functions, in particular primary, secondary and tertiary amine functions.

The basic chemical function(s) may be partially or totally neutralized, for example by adding to the composition a suitable amount of an acid such as hydrochloric acid, sulfuric acid or sulfuric acid salts, nitric acid and mono-, di- or tricarboxylic organic acids.

The preferred acids are sulfuric acid and its salts.

The organosilanes that are preferred according to the invention correspond to the formula:

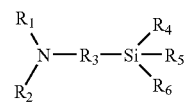

in which:
$R_4$ represents a halogen or a group OR' or $R'_1$;
$R_5$ represents a halogen or a group OR'' or $R'_2$;
$R_6$ represents a halogen or a group OR''' or $R'_3$;
and $R_1$, $R_2$, $R_3$, R', R'', R''', $R'_1$, $R'_2$ and $R'_3$ represent, independently of each other, a saturated or unsaturated, linear or branched hydrocarbon-based group optionally bearing additional chemical groups such as acid or amine groups, $R_1$, $R_2$, R', R'' and R''' also possibly denoting hydrogen, and at least two of the groups $R_4$, $R_5$ and $R_6$ being other than groups $R'_1$, $R'_2$ and $R'_3$.

Preferably, $R_1$, $R_2$, R', R'', R''' and $R'_1$, $R'_2$ and R'3 represent a $C_1$ to $C_{12}$ alkyl group, a $C_5$ to $C_{14}$ aryl group, a ($C_1$ to $C_8$) alkyl ($C_5$ to $C_{14}$) aryl group and a ($C_5$ to $C_{14}$) aryl ($C_1$ to $C_8$) alkyl group; and $R_3$ is preferably a $C_1$ to $C_{12}$ alkylene group, a $C_5$ to $C_{14}$ arylene group, a ($C_1$ to $C_8$) alkyl ($C_5$ to $C_{14}$) arylene group and a ($C_5$ to $C_{14}$) aryl ($C_1$ to $C_8$) alkylene group.

The organosiloxanes that are preferred in the compositions of the present invention may be represented by the formula:

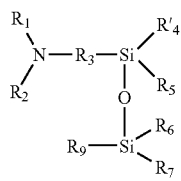

in which:

$R_1$, $R_2$, $R_3$, $R_5$ and $R_4$ are defined as above;

$R'_4$ represents a halogen or a group $OR_{11}$;

$R_7$ represents a halogen or a group $OR_{10}$ or $R''_1$;

$R_9$ represents a halogen or a group $OR_8$, $R''_2$ or $R_3NR_1R_2$;

$R''_1$, $R''_2$, $R_8$, $R_{10}$ and $R_{11}$ represent a saturated or unsaturated, linear or branched hydrocarbon-based group optionally bearing additional chemical groups such as basic solubilizing groups;

$R_{11}$, $R_{10}$ and $R_8$ also possibly denoting hydrogen.

Preferably, $R''_1$, $R''_2$, $R_8$ or $R_{10}$ and $R_{11}$ represent a $C_1$ to $C_{12}$ alkyl group, a $C_5$ to $C_{14}$ aryl group, a ($C_1$ to $C_8$) alkyl ($C_5$ to $C_{14}$) aryl group and a ($C_5$ to $C_{14}$) aryl ($C_1$ to $C_8$) alkyl group.

At least one of the groups $R_6$, $R_7$ and $R_9$ denotes a halogen or a group $OR'''$, $OR_{10}$ or $OR_8$.

Preferably, the halogen is chlorine.

The organosilicon compounds that are preferred are 3-aminopropyltriethoxysilane, 3-aminopropylmethyldiethoxysilane and 3-[bis(hydroxyethyl)amino]propyltriethoxysilane.

The compound that is particularly preferred is 3-aminopropyltriethoxysilane.

The amount of organosilicon compounds present in the composition generally represents 0.1% to 50% and preferably 1% to 20% of the total weight of the composition.

Preferably, the "nanoparticles/silicon compound" concentration ratio is from 0.05 to 2.

The content of organosilicon compounds according to the invention is determined by usual analytical methods such as 29-silicon and proton NMR spectroscopy, and by chromatography.

Although the compositions according to the invention are preferably aqueous compositions, solvents and mixtures of solvents such as an alcohol or a ketone, for example ethanol or acetone, may be used in the compositions.

In a known manner, all the compositions of the invention may contain adjuvants that are common in cosmetics, such as oils, waxes or other usual fatty substances; standard gelling agents and/or thickeners; propenetrating agents; reducing agents; emulsifiers; moisturizers; emollients, sunscreens; softeners; hydrophilic or lipophilic active agents, for instance ceramides; antifoams; antiperspirants; free-radical scavengers; surfactants; fixing or nonfixing polymers; proteins; bactericides; sequestering agents; antidandruff agents; antioxidants; basifying agents; preserving agents; fragrances; fillers; dyestuffs such as colorants and pigments; volatile or nonvolatile silicones; polyols; proteins and vitamins.

The amounts of these various adjuvants are those conventionally used in the field under consideration.

Needless to say, a person skilled in the art will take care to select the optional compound(s) added to the composition according to the invention such that the advantageous properties intrinsically associated with the composition in accordance with the invention are not, or are not substantially, adversely affected by the envisaged addition.

The compositions according to the invention are preferably used in rinse-out mode, i.e. the compositions are applied to the hair and are then left to stand for a few minutes or more before being rinsed out.

The compositions according to the invention may be in any form that is suitable for topical application, especially in the form of solutions of lotion or serum type; in the form of aqueous gels; in the form of emulsions obtained by dispersing a fatty phase in an aqueous phase (O/W) or conversely (W/O), of more or less thick liquid consistency, such as more or less unctuous milks or creams.

These compositions are prepared according to the usual methods.

The compositions according to the invention are preferably used as hair products, especially for holding the hairstyle or shaping the hair. They may also give the hair a temporary coloration, and may effectively ensure protection of the hair against the effects of UV radiation, while at the same time giving the hair holding or fixing properties.

The hair compositions according to the invention are preferably styling products such as hairsetting shampoos, gels and lotions, blow-drying lotions, and fixing and styling compositions such as lacquers or sprays.

The lotions may be packaged in various forms, especially in vaporizers, pump-dispenser bottles or in aerosol containers to allow an application of the composition in vaporized form or in the form of a mousse. Such packaging forms are indicated, for example, when it is desired to obtain a spray or a mousse for fixing or treating the hair.

The nanoparticles may also be introduced into the composition directly at the time of use.

A subject of the present invention is also the use of the composition according to the invention in a hair treatment process.

According to one embodiment of this process, the composition is applied to the rinsed or unrinsed hair, preferably in the form of a spray, either using a pump-dispenser bottle or using an aerosol.

After spraying over the entire head of hair, the composition is left to act and to dry.

The hair is then rinsed with water.

The hair may be set in the desired shape, either before the application or immediately after.

The drying time may be variable and depends on the nature of the composition.

After combing, the hair has more body and a very pleasant feel.

The invention is illustrated by the following examples:

EXAMPLE 1

The four formulations below were prepared:

| Formulation | Aminopropyltri-ethoxysilane (weight %) | Alumina nanoparticles* (weight %) | Water (weight %) |
| --- | --- | --- | --- |
| 1 | 12.5 | 0.5 | 87 |
| Comparative A | 12.5 | — | 87.5 |
| Comparative B | — | 0.5 | 99.5 |
| Control | — | — | 100 |

*Nanoparticles sold under the name "Nanotek ® aluminum oxide dispersion" by the company Nanophase Technologies Corporation.

5 g of formulation 1 described above and 5 g of the comparative formulation A are applied to two different heads of hair (European chestnut-brown hair about 20 cm long) by spraying using a spray. After leaving to stand for 15 minutes, the hair is rinsed with water.

In order to show the hair volumizing effect generated by applying the various preceding formulations, the change in the flexural rigidity of the hair after treatment of the fibers was measured by means of the "flexibility pendulum" method.

The pendulum used is of the rigid swing type with a one-second beat. This pendulum consists of a polished-brass bending bar. This bar is connected to an axle via a rod of length L=30 cm. On this rod, at a distance L'=18.5 cm from the axis of rotation, is mounted a weighted bar of mass m=47 g. The initial potential energy of the balance arm is set by its angle of inclination, written as θ.

The samples of hair are in the form of a comb of 39 fragments of hair 11 mm long bonded in parallel onto a metal support.

The measurement is performed as follows: the brass bar is released at an angle θ=30° without initial speed. At each passage through the bottom point (θ=0), the bar bends the sample of 39 hairs and loses some of its potential energy, until it comes to a complete standstill. The faster the pendulum is stopped, the more rigid are the hairs. It is considered that the loss of energy associated with the friction of the brass bar on the hairs is negligible.

To demonstrate the hair volumizing effect, a first measurement is taken before treatment, a second measurement is then taken after treatment and the number of beats required to stop the pendulum before and after treatment is then compared.

The treatment of the hairs is performed directly on the hairs mounted on the samples so as to obtain greater measurement sensitivity. For each treatment, a series of measurements is performed on 10 samples. The measurements and the drying of the samples of hair are performed at controlled temperature and relative humidity (20° C. and 45% RH).

Under the application conditions described above, it is noted that the various hair treatments induce a decrease in the number of beats required to stop the pendulum.

The different percentages of variation in the number of beats of the pendulum after application of the formulations described above are collated in the table below.

| Treatment | Formulation 1 | Comparative formulation A | Comparative formulation B |
|---|---|---|---|
| % variation in the number of beats of the pendulum after treatment | −15% ± 2% | −6% ± 1% | −10% ± 2% |

This result shows that the application of alumina nanoparticles allows the hair to be rigidified. This explains the reduced bending of the fibers observed due to the effect of gravity, visualized by a more marked volumizing of the head of hair. It is also noted that the fiber volumizing effect is increased when the nanoparticles are combined with a compound (comparative formulation B) of the type such as 3-aminopropyltriethoxysilane.

A marked effect of reduced bending of the fibers due to the effect of gravity during the use of formulation 1 compared with comparative formulation A is noted. This phenomenon is reflected visually by a more pronouced volumizing of the hairstyle after this formulation is applied. This rigidification of the fiber is amplified during the use of the organosilane. Specifically, formulation 1 gives the head of hair greater volume than the comparative formulation B, which is itself more effective than the control.

The invention claimed is:

1. A cosmetic composition comprising, in a cosmetically acceptable medium including water and/or one or more solvents,
   i) from 0.05 to 5% by weight, relative to the weight of the composition, of nanoparticles consisting of metal oxide, and
   ii) from 1 to 20% by weight, relative to the weight of the composition, of at least one organosilicon compound that is soluble in the cosmetically acceptable medium, these organosilicon compounds comprising at least two hydroxyl or hydrolyzable groups per molecule and being chosen from the compounds of formulae:

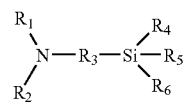

in which:
$R_4$ represents a halogen or a group OR' or $R'_1$;
$R_5$ represents a halogen or a group OR" or $R'_2$;
$R_6$ represents a halogen or a group OR''' or $R'_3$;
and $R_1$, $R_2$, $R_3$, R', R", R''', $R'_1$, $R'_2$ and $R'_3$ represent independently of each other, a saturated or unsaturated, linear or branched hydrocarbon-based group optionally bearing additional chemical groups, wherein $R_1$, $R_2$, R', R", and R''' may possibly be hydrogen also possibly denoting hydrogen, at least two of the groups $R_4$, $R_5$ and $R_6$ being other than groups $R'_1$, $R'_2$ and $R'_3$.

2. The cosmetic composition as claimed in claim 1, characterized in that the organosilicon compounds comprise three hydrolyzable or hydroxyl groups per molecule.

3. The cosmetic composition as claimed in claim 1, characterized in that the groups $R_1$, $R_2$, R', $R'_1$, $R'_2$, $R'_3$, R", R''' are chosen from $C_{1-12}$ alkyl, $C_{5-14}$ aryl, $(C_{1-8})$alkyl$(C_{5-14})$aryl and $(C_5-C_{14})$aryl$(C_{1-8})$alkyl radicals.

4. The composition as claimed in claim 1, wherein the metal oxide is selected from the group consisting of CeO, $Al_2O_3$, $TiO_2$, $BaTiO_3$, $Ba_{0.5}Sr_{0.5}TiO_3$, $SrTiO_3$, $In_2O_3$, $SnO_2$, $Sb_2O_3$, MgO, CaO, $Mn_3O_4$, $Mn_3O_4$, $MnO_2$, $MoO_3$, $SiO_2$, ZnO, and $Y_2O_3$.

5. The composition as claimed in claim 1, characterized in that the nanoparticles are less than 200 nm in size.

6. The composition as claimed in claim 1, characterized in that the "monoparticles/organosilicon compound" concentration ratio ranges from 0.05 to 2.

* * * * *